United States Patent [19]

Ren et al.

[11] Patent Number: 5,423,800
[45] Date of Patent: Jun. 13, 1995

[54] LASER SCLERAL BUCKLING METHOD AND INSTRUMENTS THEREFOR

[75] Inventors: Qiushi Ren; Gabriel Simon; Jean-Marie Parel, all of Miami, Fla.

[73] Assignee: The University of Miami, Miami, Fla.

[21] Appl. No.: 124,553

[22] Filed: Sep. 22, 1993

Related U.S. Application Data

[62] Division of Ser. No. 962,730, Oct. 19, 1992, abandoned.

[51] Int. Cl.$^6$ ............................................. A61B 17/36
[52] U.S. Cl. .................................... 606/4; 128/898
[58] Field of Search ......................... 606/4–6, 606/107; 128/898

[56] References Cited

U.S. PATENT DOCUMENTS

4,299,227 11/1981 Lincoff .................. 606/107

*Primary Examiner*—Stephen O. Pellegrino
*Assistant Examiner*—Michael Peffley
*Attorney, Agent, or Firm*—Cushman, Darby & Cushman

[57] ABSTRACT

A method of retinal re-attachment is provide including the steps of providing an optical fiber probe assembly; providing a laser system coupled to the optical fiber probe assembly for delivering at least one laser light beam to the optical fiber probe; making an incision in the conjunctiva; passing at least a portion of the optical fiber probe assembly through the incision; advancing the portion of the optical fiber probe assembly so as to separate the conjunctival-Tenon and scleral planes; positioning the portion of the optical fiber probe assembly over a retinal break area; and delivering the laser light beam from the laser system through the optical fiber probe assembly to the scleral at the locus of the retinal break area thereby to produce localized scleral shrinkage to buckle the scleral so as to relax the retinal break area. An apparatus is also provided to employ the method.

14 Claims, 8 Drawing Sheets

LASER SCLERAL BUCKLING METHOD AND INSTRUMENTS THEREFOR

This is a division of application Ser. No. 07/962,730 filed Oct. 16, 1992 now abandoned.

BACKGROUND OF THE INVENTION

1. Field of the Invention

This invention relates to retinal reattachment surgery, and more particularly to a method which uses laser induced scleral shrinkage and transscleral photocoagulation to facilitate retinal reattachment.

2. Background Information

Retinal detachment is one of the leading causes of blindness. It affects approximately one in every 15,000 people in the general population per year or an estimated 0.3% over a life-time.

Typically, retinal reattachment surgery includes the following steps: (1) conducting a thorough preoperative examination with the goal of identifying all retinal breaks and assessing any vitreous traction on the retina; (2) dissecting the conjunctiva over 360° to expose the sclera; (3) freeing the muscles of Tenon's capsule; (4) identifying and marking retinal breaks using binocular indirect opthalmoscopy and scleral depression; (5) creating a controlled injury to the retinal pigment epithelium (RPE) and retina by means of cryotherapy (cryopexy), photocoagulation, and diathermy to induce a chorioretinal adhesion (adhesion produced by wound healing) at the site of all retinal breaks; (6) when necessary, draining the sub-retinal fluid (accomplished in many instances by using a needle-shaped diathermy electrode to prevent possible choroidal hemorrhage); (7) employing all appropriate technique, such as scleral buckling and/or intravitreal gas (e.g. air, SF6, C3F8) injection or silicone oil (polydimethyl-siloxane, etc.) vitreous substitution to approximate (tamponade) the retinal breaks to the underlying retinal pigment epithelium; and finally, 8) approximating and suturing the dissected conjunctiva. Scleral buckling surgery requires significant manipulation of the eye, causes (intraoperatively) a rapid and fluctuating intraocular pressure rise ($\geq 200$ mmHg), and is time consuming. Rehabilitation from such surgery is from one to four days. Furthermore, scleral buckling has been associated with recurrent proliferative vitreoretinopathy (PVR), a complication that is difficult to treat.

The purpose of the buckle is to create enough scleral indentation (bump) for the choroid to approximate the detached retina following subretinal fluid drainage. Most buckling surgical procedures require a great deal of surgical incisions and dissections to position the implant that has to be sutured to the sclera in order to create a stable and adequate buckling effect. The implant, also known as an exoplant, may be made, for example, of several forms of silicone (solid, sponge or foam) rubber, of hydrogels or, in poor countries, fascia lata.

Since a high percentage of retinal detachment patients are myopic, conventional buckling surgery may induce more myopia and astigmatism since the surgery has a tendency to elongate the total length of the eye (increase the eye's axial length). More importantly, current surgical techniques have very limited applications to some difficult pathological conditions such as staphylomata, caused by high myopia, where the sclera is very thin and can hardly support dissections and sutures.

Chorioretinal adhesion is induced either by RF diathermy, cryopexy or photocoagulation. RF diathermy has been shown to cause more postoperative complications than the other two techniques, and has largely been abandoned for treatment of retina detachments. The cryogenic probes ($-70°$ to $-90°$ C. tip temperature, application time of $\approx 5s$) used in retinal cryopexy are bulky, inflexible, and produce unnecessary large damage to scleral tissue and underlying structures. Retinal photocoagulation is the preferred method to produce chorioretinal adhesion normally performed *ab interno*, by focusing the energy of a continuous-wave (cw) Argon, a cw Krypton, or a cw diode laser, etc., through the patient's cornea and pupil, onto the retina. The laser delivery systems in common use are the operating microscope and the indirect ophthalmoscope for intraoperative treatment, when the patient is in the supine position, and the slit-lamp for postoperative treatment, when the patient is in the sitting position. Should an intraocular procedure such as vitrectomy or retinotomy be required to unfold and re-approximate the retina to the choroid, then retinal photocoagulation is normally performed intraoperatively using a fiber optic probe inserted in the vitreous cavity, a procedure known as "endophotocoagulation". Recently, intraoperative and postoperative retinal photocoagulation has also been performed *ab externo* (transsclerally) using the energy produced by a cw Nd:YAG laser (Neodymium: Yttrium Aluminum Garnet; wavelength$=1.06$ $\mu$m or a C. W. Diode Laser (808 nm)) conducted through a fiber optic probe applied to the sclera overlying the retina break.

Conventional scleral buckling procedures require extensive surgical manipulations, implantation of a device and may require the use of an expensive laser system to produce chorioretinal adhesion. Since mechanical buckling increases the length of the eye, as noted above, a patient with a successfully reattached (and intact) retina, may nevertheless require spectacles or contact lenses to regain adequate vision.

Accordingly, it can be appreciated that a need exists to provide a simplified and more advantageous surgical method of retinal reattachment using light to shrink scleral tissue to produce a "buckle".

SUMMARY OF THE INVENTION

An object of the present invention is to provide a method which simplifies retinal reattachment surgery, thus, reducing surgical time and minimizing patient trauma.

In accordance with the principles of the present invention these and other objectives are obtained by providing a method of retinal reattachment including the steps of providing an optical fiber probe assembly; providing a laser system coupled to the optical fiber probe assembly for delivering at least one laser light beam to the optical fiber probe; making an incision in the conjunctiva; passing at least a portion of the optical fiber probe assembly through the incision; advancing the portion of the optical fiber probe assembly so as to separate the conjunctival-Tenon and scleral planes; positioning the portion of the optical fiber probe assembly over a retinal break area; and delivering the laser light beam from the laser system through the optical fiber probe assembly to the sclera at the locus of the retinal break area thereby to produce localized scleral shrinkage to buckle the sclera so as to relax the vitreous traction over the retinal break area.

It is a further object to provide an apparatus for use in performing the inventive method. In accordance with the principles of the present invention, the further object is achieved by providing an apparatus for surgically treating the eye, including a laser system having a plurality of lasers for producing beams of laser light at various frequencies; means for selecting particular beams of laser light from the laser system; and a fiber optic probe assembly for receiving at least one of the beams of laser light. The fiber optic probe assembly has at least one, or a plurality of monofilament light guides and has an end portion sized so as to be insertable into an incision near the eye for delivering at least one of said beams of laser light to localized portions of the eye.

Other objects, features and characteristics of the present invention, as well as the methods of operation and functions of the related elements of the structure, and the combination of the parts and economics of manufacture, will become more apparent upon consideration of the following detailed description and appended claims with reference to the accompanying drawings, all of which form a part of this specification.

DETAILED DESCRIPTION OF THE PRESENTLY PREFERRED EXEMPLARY EMBODIMENT

Figure 1:
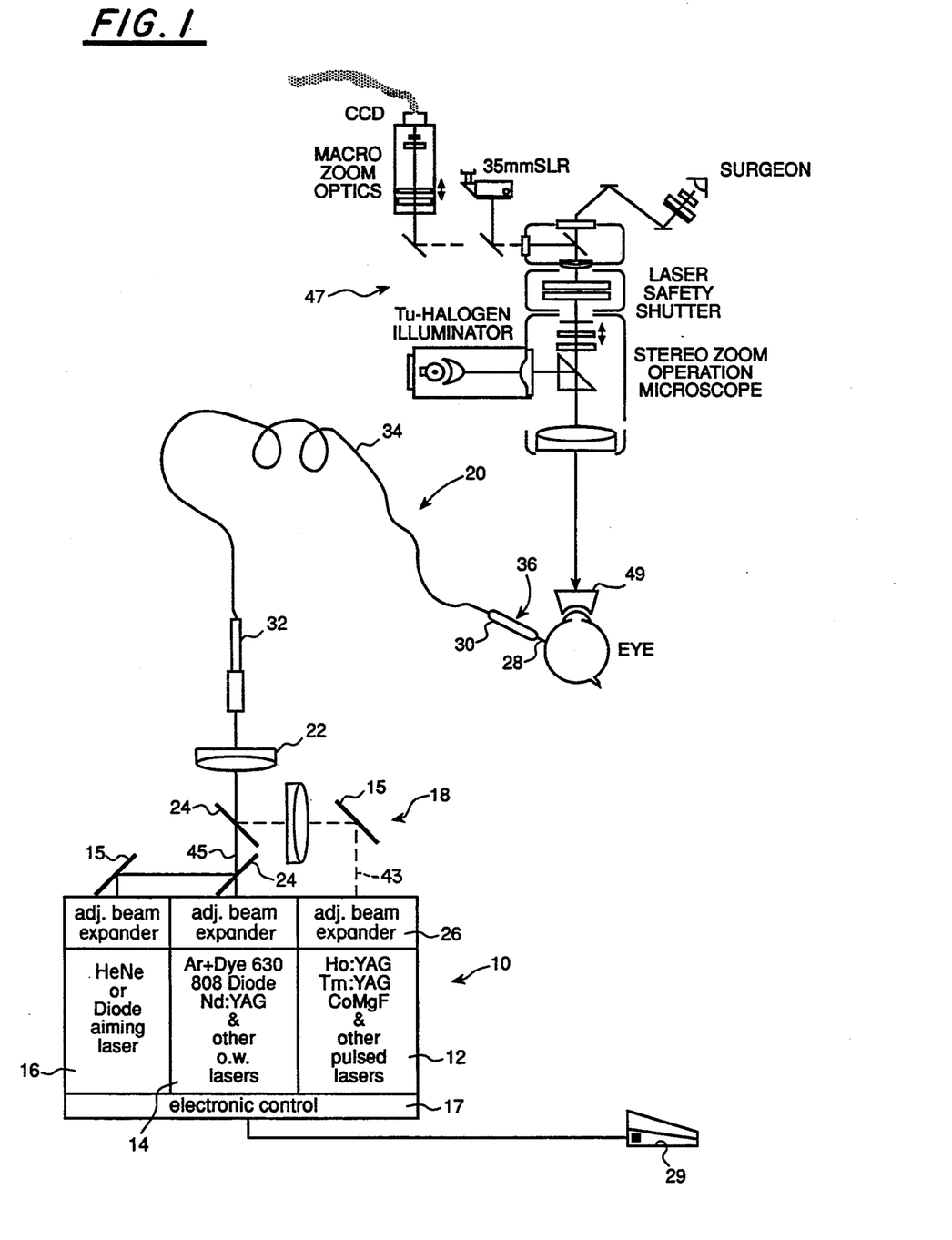
FIG. 1 is a schematic illustration of the laser system for performing laser buckling surgery, provided in accordance with the principles of the present invention.
Figure 2:
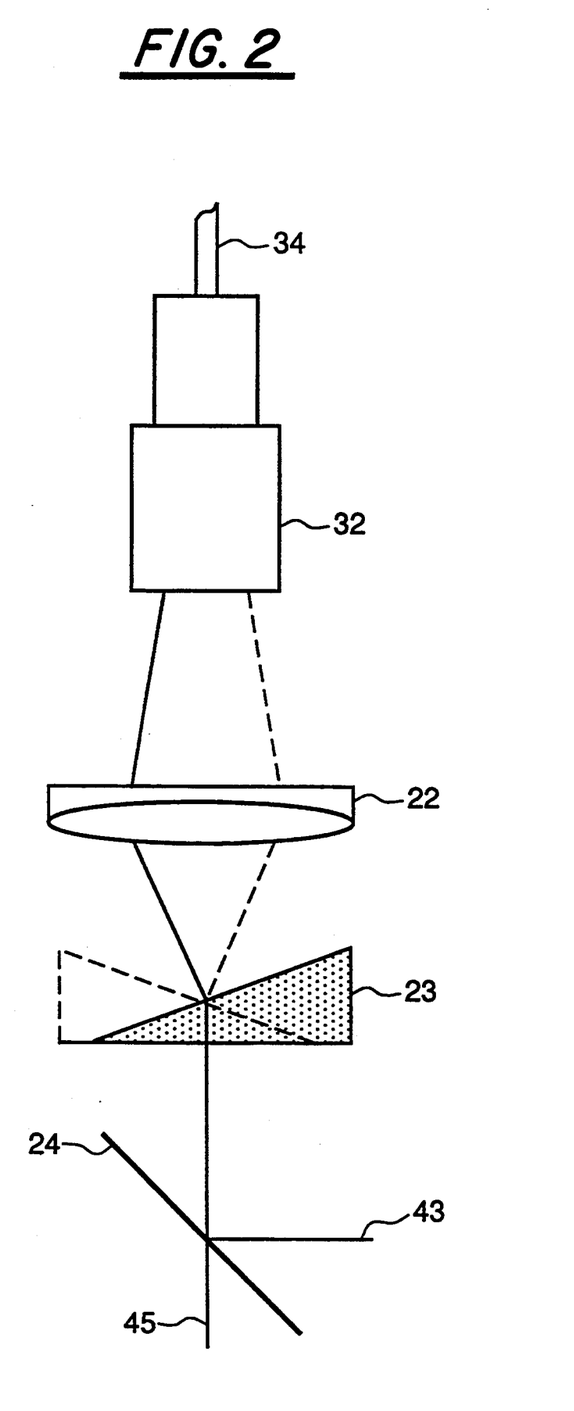
FIG. 2 is a schematic view of a beam splitting device for directing a laser into one of several optical fibers provided in accordance with the principles of the present invention.
Figure 3:
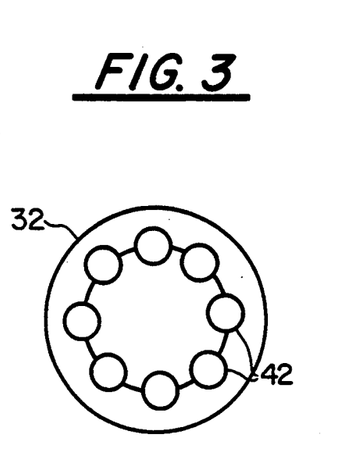
FIG. 3 is a front view of an end portion of a fiber optic probe of the present invention.

The laser system 10, for performing the inventive method of retinal reattachment surgery is schematically shown in FIGURE. 1. The laser system 10 is preferably composed of two or more different lasers 12, 14 and 16 coupled to a common electrical control unit 17, an optical beam launching system 18, and a single, detachable fiber optic probe 20. The optical beam launching system 18 includes a dichroic beam combiner 24 which is necessary when more than one laser is required and is utilized to combine both laser beams thereof that are focussed into the proximal end of the fiber optic probe 20 with condensing lenses 22. Reflecting mirrors 15 are used to change the direction of emitted beams. A rotating prism 23 may be disposed between the combiner 24 and the condensing lens 22, as shown in FIG. 2. Rotating the prism 23 on the laser beam axis rotates the deflected beam around a circle. Individual optical fibers 42 (FIG. 3) in plug 32 are aligned on a circle of equal diameter, corresponding exactly to the prism deflecting angle. A step-motor can be used to align the focussed beam into any one fiber 42. The step-motor is mechanically connected so that the laser beam "jumps" from one fiber to another. Thus, the surgeon can selectively make a single shrinkage or coagulation spot with a multi-filament fiber, without having to reposition the probe, which will become more apparent below.

Figures 4, 4A, 5, 6:
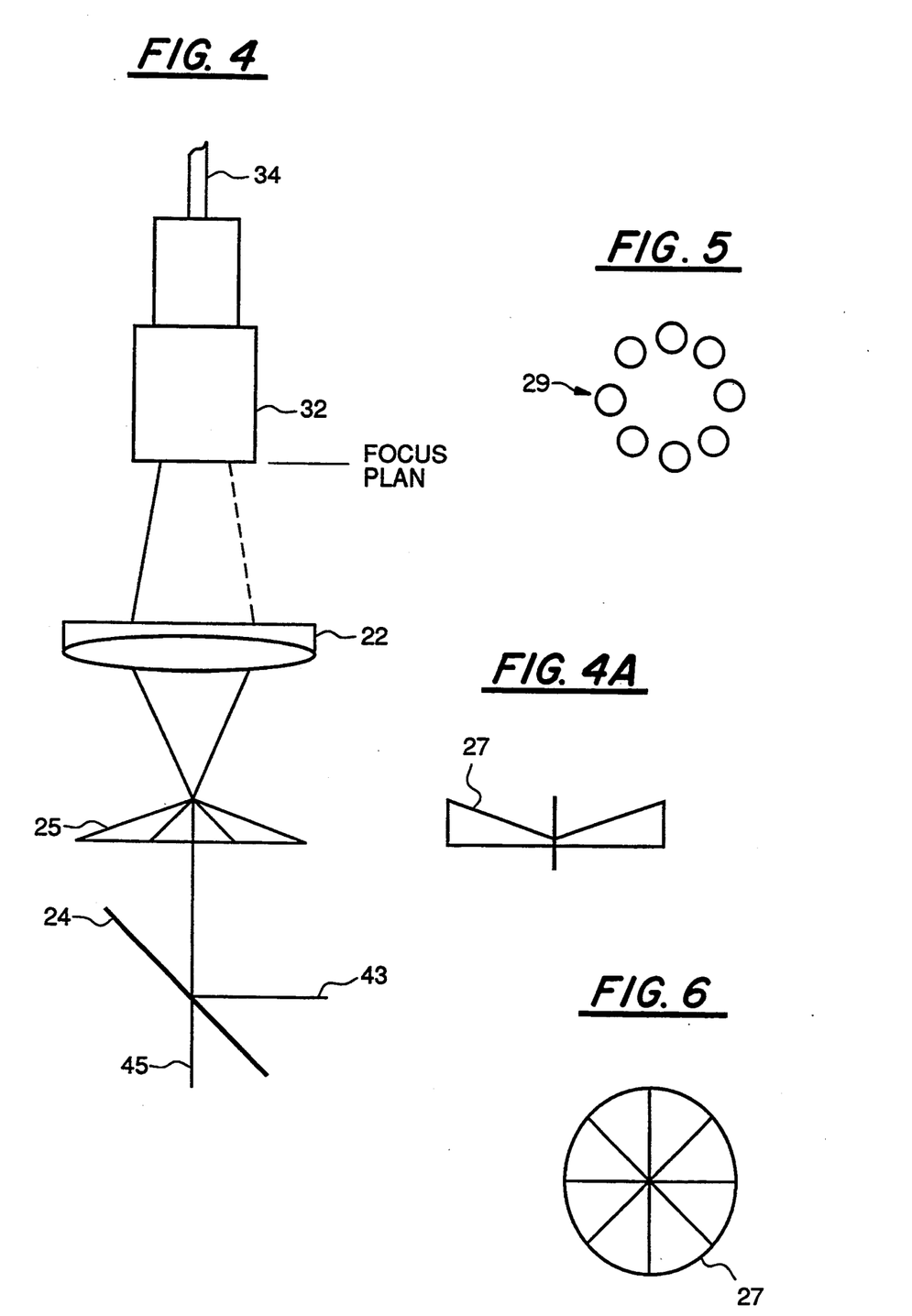
FIG. 4 is a schematic view of a beam splitting device for directing a laser into several of optical fibers.
FIG. 4A is a schematic view of a negative polyprism which may be disposed in the device of FIG. 4.
FIG. 5 is a beam pattern as the focus plan of FIG. 4.
FIG. 6 is a front view of an 8-facet polyprism.

Alternately, a positive polyprism 25 or a negative polyprism 27 can be disposed between the combiner 24 and the condensing lens 22, as shown in FIG. 4. The polyprism divides the laser beam into a plurality of beams. Each sub-beam is then centered on an individual fiber 42. An 8-facet polyprism is shown in FIG. 6. The number of sub-beams to be focussed is equal to the number of facets. For example, the 8-facet polyprism will produce a focus plan for eight optical fibers 29, as shown in FIG. 5. The polyprism deflection angle is a function of the polyprism angle and its index of refraction. Using this arrangement, the surgeon may use a plurality of outputs beams 43 (FIG. 7) at once. Naturally, the fiber bundle composing fibers 42 can include one or more sets of eight fibers. The step-motor aligns the laser sub-beams over a selected array of eight fibers.

Figure 13A:
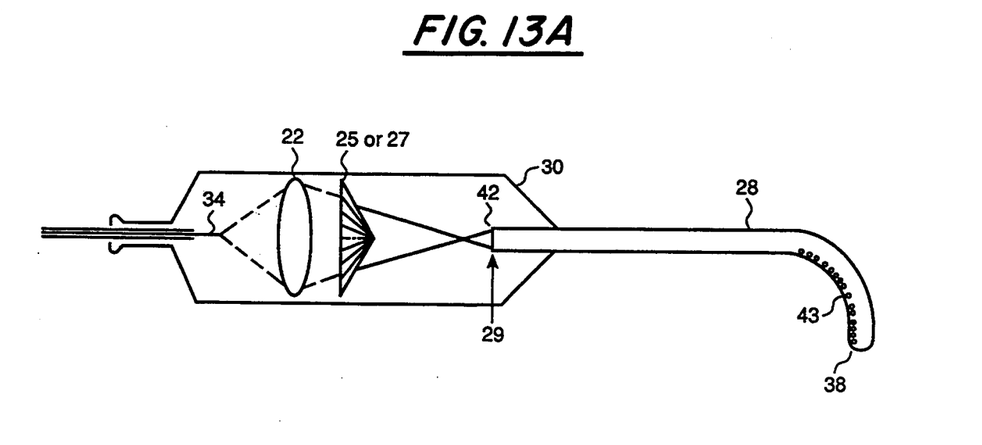
FIGS. 13a—13c are front views of an endoprobe including polyprismatic devices disposed in a handle thereof.
Figure 13B:
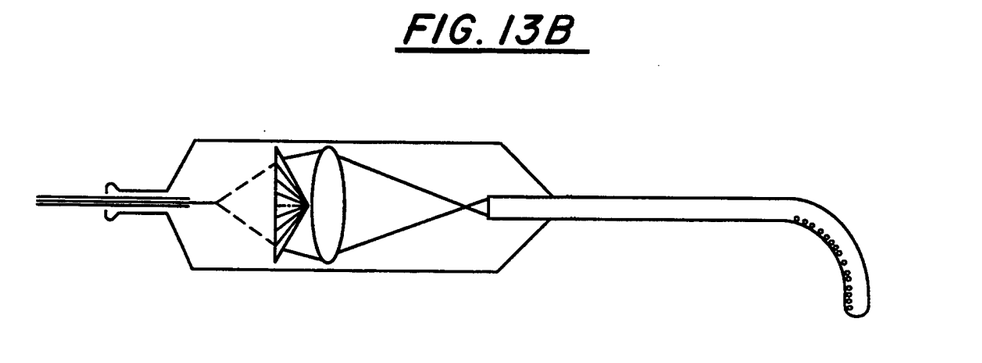
Figure 13C:
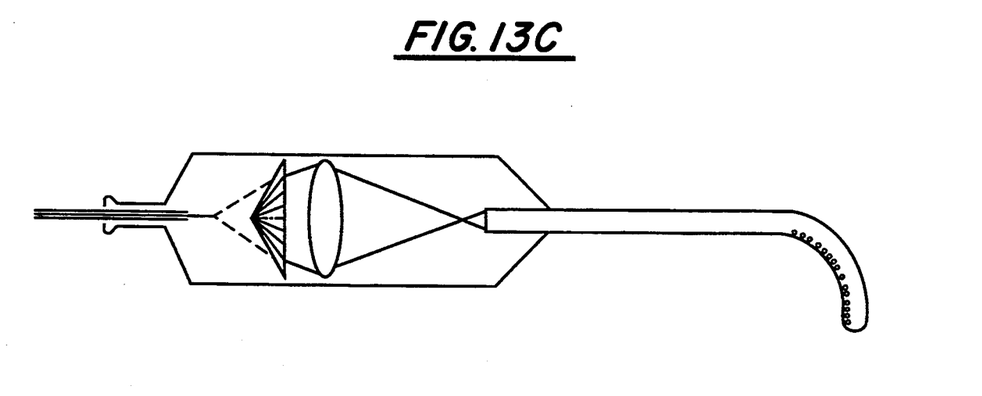

Alternately, as shown in FIGS. 13a—13c, the condensing lenses and prisms can be provided within the handle 30 of the endoprobe 36, which will become more apparent below. FIGS. 13a–13c each show an optical fiber bundle 34 disposed within handle 30. When optical elements such as lens 22 and the polyprisms 25, 27 are disposed within the handle, the optical fiber bundle 34 need only contain a monofilament fiber to conduct the light emitted from the laser system 10. As shown in FIGS. 13a to 13c, the position of the condensing lens 22 and polyprismatic device 25 or 27 can be reversed, producing the same effect, namely the formation of a plurality of sub-beams focused on probe tip 28 which contains a symmetric arrangement of individual fibers 42 which numbers match the number of facets of the polyprismatic device selected. In addition, the same optical effect is obtained by reversing the position of the polyprism.

A third laser 16, emitting a visible beam (e.g. HeNe ion laser, 670 nm Diode laser) may be included in the laser system 10 to facilitate aiming during surgery. Beam focus and numerical aperture matching are obtained by using one or two adjustable beam expanders 26. Activating the lasers 12 and 14 is done by the surgeon with a two-function foot pedal.

Figure 7:
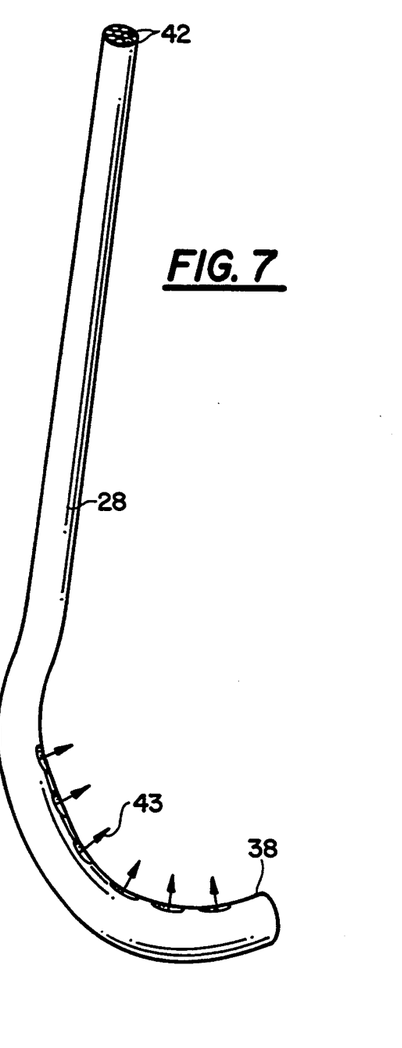
FIG. 7 is a side view of the laser endoprobe provided in accordance with the principles of the present invention.
Figure 8:
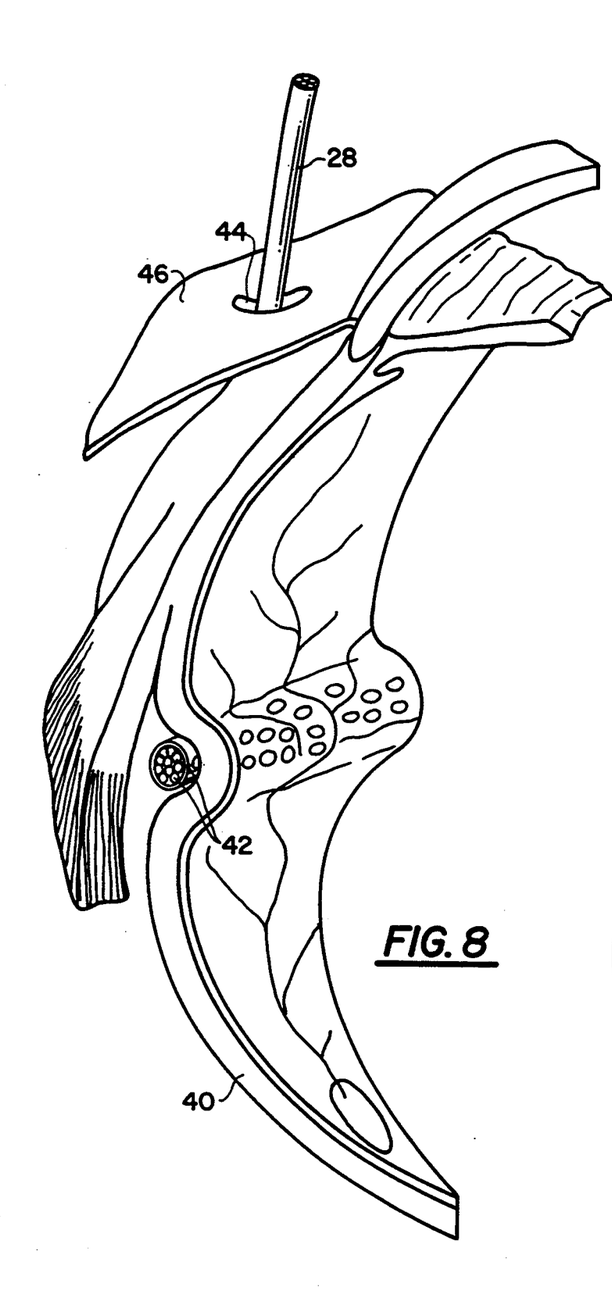
FIG. 8 is a partial view of an eye showing the laser endoprobe positioned over a retinal break area thereof in accordance with the invention.

The fiber optic probe 20 of the present invention is shown in FIGS. 7 and 8. Preferably, the probe is disposable or sterilizable. The probe 20 includes a plug-in, prefocussed, optical connector 32 at a distal end thereof. An optical fiber bundle 34 having a diameter preferably in the range of 50 to 900 micrometers is coupled to the optical connector 32. The other end of the optical fiber bundle 34 is coupled to a laser endoprobe 36. The laser endoprobe includes a suitably bent tip 28 affixed to a handle 30. An optional accessory coaxial sleeve (not shown) may surround the fiber to provide for aspiration (e.g. blood) and/or for infusion of fluids to for example, cool the scleral surface and minimize laser transmission losses at the fiber-tissue interface. The optical fiber bundle 34 may be composed of one or a plurality of commercially available low OH silica and ZrF4 (Zirconium Fluoride) monofilament step-index fiber. The laser endoprobe tip 28 preferably has a diameter of approximately 1 mm and includes a curved tip portion 38, for ease of placement through the orbital space over the sclera 40 (FIG. 8). The curved tip portion 38 has a radius of curvature of approximately 13 mm. The curved tip portion 38 may be further bent to allow for a row of multiple treatment spots to be placed simultaneously or sequentially and circumferentially around the curvature. The laser endoprobe 36 may contain several optical fibers 42, preferably having diameters between 20 to 300 $\mu$m to produce a row of treatment spots, as shown in FIG. 8.

Figure 9:
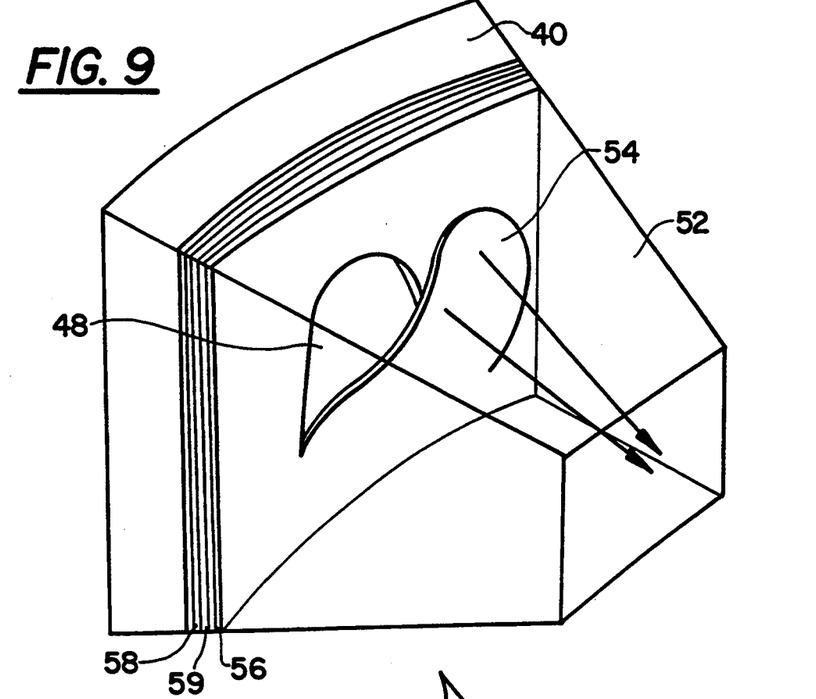
FIG. 9 is an enlarged view of the area of a retinal tear.
Figure 11:
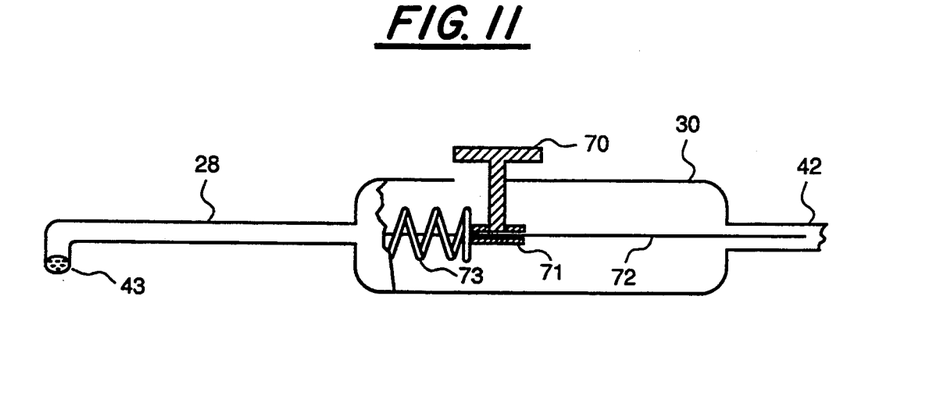
FIG. 11 is front view of an endoprobe for perforating the sclera and choroid, provided in accordance with the principles of the present invention.
Figure 12:
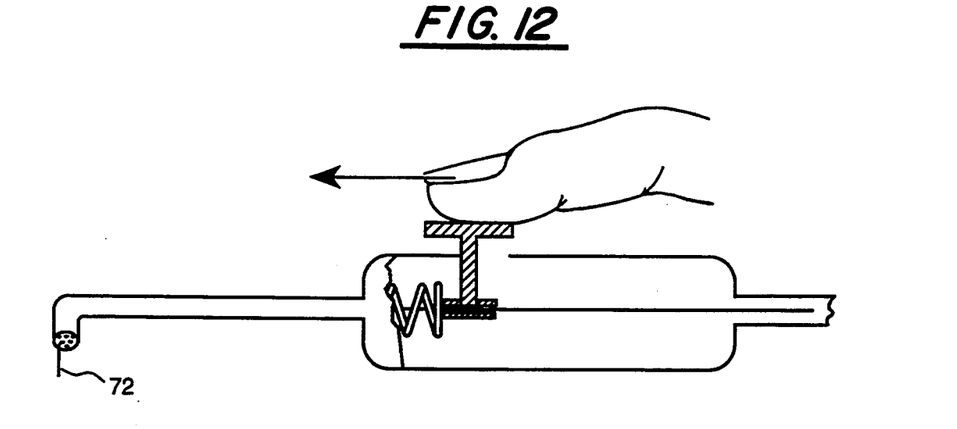
FIG. 12 is a front view of the endoprobe of FIG. 11 being actuated to permit a fiber to protrude from an end portion thereof.
Figure 12A:
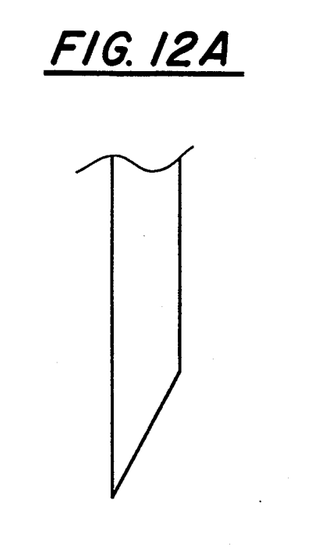
FIG. 12A is an enlarged view of a monofilament fiber which may be provided for the endoprobe of FIG. 12.
Figure 12B:
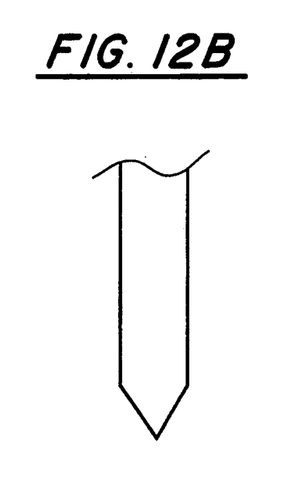
FIG. 12B is an enlarged view of an alternate monofilament fiber for the endoprobe of FIG. 12.

FIGS. 11 and 12 show an endoprobe 36 having a perforating feature. Conventionally, when sub-retinal fluid needs to be removed, the surgeon perforates the sclera and choroid with a needle-shaped diathermy tip. The diathermy is needed only to stop bleeding when it occurs. In the illustrated embodiment, this function is provided by a monofilament fiber 72, connected to the laser photocoagulation system 14. The monofilament fiber has a diameter of 50 $\mu$m or less and has a cone or needle-shaped end, as shown in FIG. 12. The monofilament fiber 72 is disposed within the endoprobe 36. The handle 30 includes a fiber holder 71 affixed to an advancing lever 70. A compression spring 73 is disposed between the fiber holder and an end of the handle 30. Advancing the lever 70 forward, compresses spring 73 pushing the fiber holder 71, therefore enabling the monofilament fiber 72 to protrude from the probe tip 28 to perforate the eye coats 40, 58 and 59 (FIG. 9). Should any hemorrhage occur, the surgeon merely pushes the foot pedal 29 and the laser photocoagulate this region. Preferably an Argon-ion gas laser emitting at 488 nm and or 514.5 nm or a quasi-cw frequency doubled Nd:YAG laser emitting at 512 nm is used because these lasers work close to the absorption peak of hemoglobin. The spring 73 retracts the spring as soon as lever 70 is released. The same probe is equipped with fibers 43 allowing collagen shrinkage (for buckling) and photocoagulation (to create the chorio-retinal adherence) which will become more apparent below. Sub-retinal fluid can also be removed by switching the laser system to a cutting laser (e.g. Thulium YAG laser or pulse laser), directing the laser through one of the fibers in the fiber bundle 34 at a proper wavelength to create a hole in the sclera and choroid.

A beam 43 of a pulse, or of an electo-shutter equipped quasi-cw or cw laser emitted from laser 12 at about 1.3 $\mu$m to 2.6 $\mu$m wavelength with a pulse duration of 100 microseconds to about 100 milliseconds and an energy of about 5 to 1,000 mJ (e.g. Holmium:YAG, Thulium:YAG laser, cw HF laser or cw DF laser) is transmitted through the optical fiber bundle 34 and through one or more of the optical fibers 42. The beam 43 is used to generate a localized "buckling" effect by shrinking the sclera 40 at one or more locations over the retinal break. When required, one or several treatment rows can be made around the eye's equator to enhance the buckling effect. These rows may be made individually using the laser endoprobe 36 having a single fiber (not shown) or a probe containing several fibers (FIG. 7).

Activating laser 14, a cw or quasi-cw laser emitting between 50 mW to 10 W of power at wavelengths between $\approx 0.60$ $\mu$m to $\approx 2.6$ $\mu$m, (e.g. 1064 nm Nd:YAG, a diode laser (e.g. 808 nm), approximately 700–1000 nm tunable Titanium Sapphire laser or a tunable pumped dye laser (approximately 580 to 1000 nm)) permits the same fiber optic probe 20 to be used to create a chorioretinal adhesion around the site of the retinal break, as will be detailed below.

Figure 10:
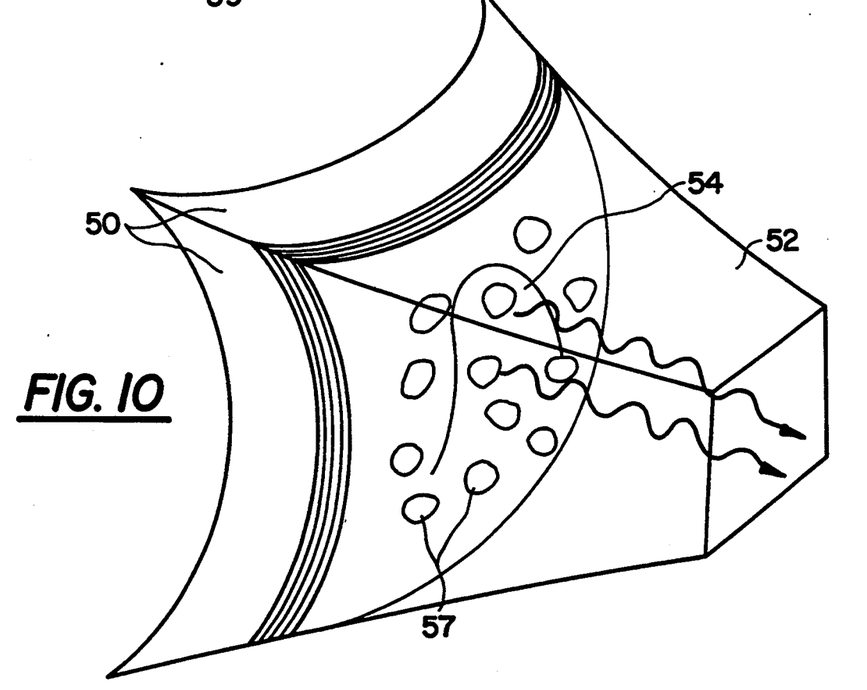
FIG. 10 is an enlarged view of the area of retinal tear after utilizing the shrinkage process of the present invention.

To reattach the retina, in accordance with the principles of the present invention, an incision 44, slightly larger than 1 mm wide, is made in the conjunctiva 46. It should be noted that the procedure of the present invention, so called "Laser Buckling", is very different from conventional implant-induced buckling effect. With "Laser Buckling", a full dissection of the conjunctiva 46 is not required, since the 1 mm diameter laser endoprobe tip 28 can be passed through the conjunctival incision 44, and advanced forward while slightly turning the endoprobe left to right to separate the conjunctival-Tenon and scleral planes. Next, the endoprobe 36 is positioned over the retinal break area 48 by the surgeon using a microscope system, generally indicated at 47. The surgeon may require a contact lens 49 be placed over the patient's cornea to view the retinal area to be treated. Alternatively, may also use an indirect ophthalmoscope and a hand-held focussing lens (not shown) to view the retinal area to be treated. The pulsed laser beam 43 is then delivered through the fiber optic probe 20 and applied to the eye scleral coats to produce a localized ¾ to 4/5 depth scleral shrinkage (FIG. 10). A scleral "buckling" effect results from laser-induced collagen shrinkage 50. Traction of the vitreous 52 (shown by the arrow in FIG. 9) on the retina that produced the tear becomes relaxed as the shrinkage process buckles the scleral coat inward and brings the retinal pigment epithelium 59 (RPE) into contact with the retinal flap 54 (FIG. 10). If needed, a fluid-gas exchange or a silicone oil vitreous substitution may be performed to firmly tamponade the retina before inducing chorioretinal adhesion by laser photocoagulation using either conventional techniques or the same probe coupled to another laser. As a fiber optic probe will be applied at the site of the retinal break to shrink the sclera, one can easily photocoagulate the site transsclerally by connecting the same probe to another laser to produce laser adherence locations 57. For this portion of the treatment, a cw or quasi-cw laser 14 emitting a beam 45 at a wavelength between 0.65 $\mu$m and 2.5 $\mu$m is preferably employed. The optimal wavelength is selected to facilitate penetration through the sclera 40 and absorption by the retinal pigment epithelium 59. As an alternative to using the cw Nd:YAG laser 14 at 1.06 $\mu$m and 1.3 $\mu$m wavelengths, other lasers may alternatively be employed for such adhesion (e.g., a quasi cw 808 nm Diode laser, a cw Argon-ion pumped dye laser tuned between 600–1000 nm, an Alexandrite laser tuned between 720 to 800 nm or a tunable Titanium Sapphire laser tuned between 690 to 1000 nm).

The laser induced "buckling" effect is caused by a localized contraction of the upper layers of the sclera 40. The contraction occurs when the scleral collagen reaches a temperature of about 50° to 75° C. Since the pulse duration and penetration depth of the laser energy can be precisely selected, thermal conduction can be controlled to limit side effects such as excessive thermal damage, retinal damage, shockwave damage, etc. Hence, temperature is highest externally and the deeper scleral layers remain at relatively low temperature (below 42° C.). Thus, the underlying tissues and structures such as the choroid 58 and retina 56, are not impaired. The amount of scleral contraction is a function of the laser energy radiant exposure ($J/cm^2$ in the tissue absorption characteristics), the number of pulses, and the geometric distribution of the laser treatment spots on the eye.

The laser parameters used in the "Laser Buckling" method of the present invention depend upon the laser employed. For example, using a pulsed, solid-state Ho:YAG laser 12 (Holmium:YAG) the parameters are: wavelength $=2.10$ $\mu$m, pulse duration $\approx 250$–350 $\mu$s, energy per pulse$=0.05$ to $\approx 0.3J$, repetition rate$=1$ to $\approx 5$ HZ with a 300 nm diameter monofilament fiber optic probe.

Preliminary histology of the method of the present invention indicates no evidence of tissue charring or choroidal and/or retinal damage when adequate laser parameters are used.

Figure 14:
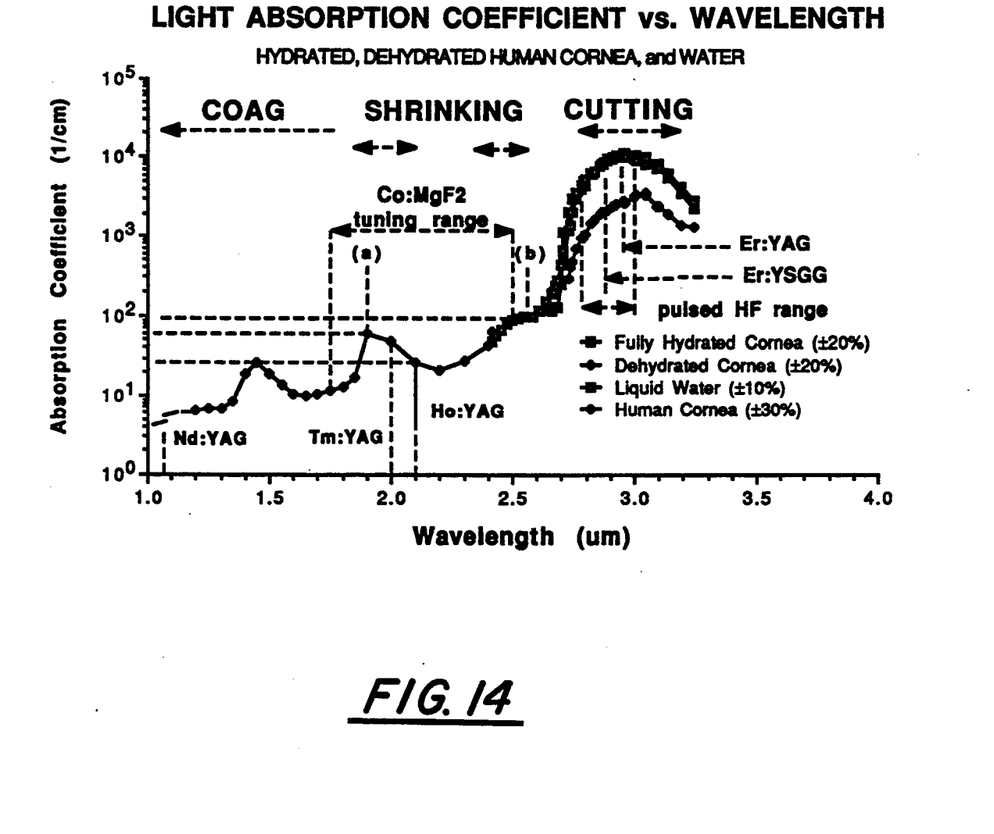
FIG. 14 is a graph showing light absorption coefficient vs. wavelength.

As shown in FIG. 14, scleral and muscle shrinkage is best performed at wavelengths from 1.3 to 2.6 $\mu$m because scleral tissue, like corneal tissue, is mainly composed of water ($\geq 75\%$), the main photon absorber at these wavelengths.

Apart from the Holmium laser emitting at 2.1 $\mu$m with a penetration depth of 360 $\mu$m, several other laser sources may be used to perform "Laser Buckling". For example, a Thulium:YAG laser produces a 2.01 $\mu$m wavelength that has a shorter tissue penetration depth ($\approx 160$ $\mu$m). This feature may be advantageous for patients having a very thin sclera. Tissue penetration depth can be selected using a Co:MgF2 (Cobalt Magnesium Fluoride) laser since it can be tuned between $\approx 1.8$ and $\approx 2.4$ $\mu$m wavelengths. Another laser, the line tunable cw Hydrogen Fluoride (HF) laser manufactured by Helios, can also be used for the "Laser Buckling" process since it can be adjusted to produce wavelengths from $\approx 2.3$ to $\approx 3.0$ $\mu$m. The foregoings are just a few examples of commercially available lasers or black body radiators which may be employed for the "Laser Buckling" process of the present invention. Of course, other lasers having similar operating parameters may be employed. Compared with conventional implant techniques, the process and apparatus of the present invention are less traumatic, reduce morbidity and do not increase eye-length. Further, should a 360° application be needed, scleral shrinkage will slightly reduce the length of the eye, hence myopic patients should require less refractive correction post-operatively. The procedure of the present invention may be used to treat high myopia, including staphyloma cases.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims. For example, the laser system 10 may be used to shrink and coagulate other eye tissues as well as tissue of other organs of the body such as in orthopedics, ortholaryngologists and neuro-surgery.

What is claimed is:

1. A method of retinal re-attachment comprising the steps of:
   providing an optical fiber probe assembly;
   providing a laser system coupled to said optical fiber probe assembly for delivering at least one laser light beam to said optical fiber probe;
   making an incision in the conjunctiva;
   passing at least a portion of said optical fiber probe assembly through said incision;
   advancing said portion of said optical fiber probe assembly so as to separate the conjunctival-Tenon and scleral planes;
   positioning said portion of said optical fiber probe assembly over a retinal break area; and
   delivering said at least one laser light beam from said laser system through said optical fiber probe assembly to the sclera at the locus of said retinal break area thereby to produce localized scleral shrinkage to buckle said sclera so as to relax said retinal break area.

2. The method according to claim 1, further comprising the step of using laser photocoagulation at said retinal break area to achieve chorioretinal adhesion, after the step of delivering said at least one laser light beam.

3. The method according to claim 1, wherein said step of providing an optical fiber probe assembly includes providing an optical fiber member having first and second ends, said first end being coupled to said laser system, said second end being coupled to a laser endoprobe.

4. The method according to claim 3, wherein said step of providing a laser endoprobe includes providing at least one optical fiber element disposed within said laser endoprobe and coupled to said second end of said optical fiber member.

5. The method according to claim 3, wherein said step of providing a laser endoprobe includes providing a laser endoprobe having a generally circular cross-section and a diameter of approximately 1 millimeter.

6. The method according to claim 3, wherein said step of providing a laser endoprobe includes providing a laser endoprobe having a curved end portion.

7. The method according to claim 6, wherein said step of providing a laser endoprobe includes providing said endoprobe including an end portion having a radius of curvature of approximately 13 millimeters.

8. The method according to claim 1, wherein said step of providing a laser system includes providing one of a Holmium: Yttrium Aluminum Garnet, a tunable Cobalt Magnesium Fluoride laser, a cw HF laser and a cw DF laser for generating said light beam.

9. The method according to claim 1, wherein said step of providing a laser system includes providing a Thulium: Yttrium Aluminum Garnet laser for generating said light beam.

10. The method according to claim 8, wherein said step of providing said laser system further includes providing a second laser for emitting a visible beam of light to facilitate aiming.

11. The method according to claim 8, wherein said step of providing a laser system further includes providing a second laser emitting a visible beam of light to facilitate aiming.

12. The method according to claim 2, wherein said step of providing a laser system includes providing one of a Neodymium: Yttrium Aluminum Garnet laser, a diode laser and a tunable Argon-ion pumped dye laser for said step of using laser photocoagulation.

13. The method according to claim 1, wherein the step of producing localized scleral shrinkage occurs at a temperature of about 50 to 75 degrees Celsius.

14. The method according to claim 1, wherein the step of providing a laser system includes providing means for directing light to said optical fiber probe assembly.

* * * * *